(12) United States Patent
Hotta et al.

(10) Patent No.: US 6,776,029 B2
(45) Date of Patent: Aug. 17, 2004

(54) OIL CONTENT MEASURING DEVICE AND REFRIGERATION SYSTEM USING THE SAME

(75) Inventors: Tadashi Hotta, Okazaki (JP); Yukikatsu Ozaki, Gamagori (JP); Toshio Hirata, Haguri-gun (JP)

(73) Assignees: Denso Corporation, Kariya (JP); Nippon Soken, Inc., Nishio (JP)

(*) Notice: Subject to any disclaimer, the term of this patent is extended or adjusted under 35 U.S.C. 154(b) by 0 days.

(21) Appl. No.: 10/271,678

(22) Filed: Oct. 15, 2002

(65) Prior Publication Data

US 2004/0069051 A1 Apr. 15, 2004

(51) Int. Cl.$^7$ .......................... G01N 33/30; G01N 37/00
(52) U.S. Cl. .................... 73/61.41; 73/61.43; 73/61.46; 73/61.47; 73/61.61; 73/61.78
(58) Field of Search ........................ 73/61.41, 61.43, 73/61.46, 61.47, 61.61, 61.78

(56) References Cited

U.S. PATENT DOCUMENTS

| 3,686,954 A | * | 8/1972 | Moll ......................... 73/865.9 |
| 5,315,376 A | * | 5/1994 | Wada et al. ................ 356/432 |
| 6,302,654 B1 | * | 10/2001 | Millet et al. ................ 417/63 |
| 6,505,475 B1 | * | 1/2003 | Zugibe et al. .............. 62/192 |

FOREIGN PATENT DOCUMENTS

| JP | 62-131989 | * | 6/1987 | ................ 73/1.16 |
| JP | 3-233268 | * | 10/1991 | ................ 62/125 |
| JP | 5-5495 | * | 1/1993 | |
| JP | 5-256806 | | 10/1993 | |
| JP | 9-96618 | | 4/1997 | |
| JP | 200-105032 | * | 4/2000 | ................ 73/40 |

OTHER PUBLICATIONS

"Measurement of Refrigerant Solubility in Refrigerating Machine Oil By Capacitance Sensor", Transaction of the Japan Society of Refrigerating and Air Conditioning Engineers, vol. 16, No. 3 (1999).

* cited by examiner

Primary Examiner—Daniel S. Larkin
(74) Attorney, Agent, or Firm—Harness, Dickey & Pierce, PLC

(57) ABSTRACT

An oil content measuring device measures the oil content of a refrigerant in a supercritical or a vapor phase state. A refrigeration system uses the oil content measuring device. The oil content measuring device has an electrostatic capacity measuring device for measuring an electrostatic capacity of the refrigerant containing a refrigerating machine oil, a density measuring device for measuring a density of at least one of the refrigerant and the refrigerating machine oil, a computing device for performing a computation on correlation characteristics between the electrostatic capacity and an oil content which indicates the ratio of the amount of the refrigerating machine oil to the amount of the refrigerant containing the refrigerating machine oil, using the density measured by the density measuring device. An oil content determining device determines an oil content at the measuring time from an electrostatic capacity using the correlation characteristics obtained by the computing device.

10 Claims, 8 Drawing Sheets

OIL CONTENT MEASURING DEVICE AND REFRIGERATION SYSTEM USING THE SAME

CROSS REFERENCE TO RELATED APPLICATION

This application is based upon Japanese Patent Application No. 2001-206891, filed on Jul. 6, 2001.

BACKGROUND OF THE INVENTION

1. Field of the Invention

The present invention relates to an oil content measuring device for measuring a refrigerating machine oil within a refrigerant used in a refrigerating machine of an air conditioner, and to a refrigeration system using the same.

2. Description of the Related Art

A refrigerating machine oil (i.e., a lubricating oil) for lubricating a refrigerant compressor in a refrigerating machine is important for ensuring the long-lasting durability of a compressor. Therefore, it becomes very important to know the amount of refrigerating machine oil in the refrigerant. More substantially, how much of the refrigerating machine oil is contained in the refrigerant compressor itself.

As a conventional technology for measuring the amount of a refrigerating machine oil, "Measurement of Solubility of Refrigerant in Refrigerating Machine Oil by Electrostatic Capacity" in Transactions of the Japan Society of Refrigerating and Air Conditioning Engineers, vol. 16, No. 3 (1999) has been well known in the art.

Such a conventional measuring method utilizes the difference in electrostatic capacities between the refrigerating machine oil and the refrigerant. As the electrostatic capacity in a dissolved state of the refrigerating machine oil and the refrigerant have a correlation with the solubility of the refrigerant (it can be defined as an oil content, so it will be referred to as an oil content hereinafter), the above method obtains the oil content by measuring the electrostatic capacity.

In the above conventional method, the relation between the oil content and the electrostatic capacity is obtained using temperature as a parameter and is then prepared as known data, followed by performing a measurement of electrostatic capacity by an electrostatic capacity sensor with the known data to obtain an actual oil content. Therefore, it is a cost effective measurement.

However, in the above conventional method, a target of the measurement is refrigerant in a liquid phase state and it only considers the change in electrostatic capacity using temperature as a parameter to obtain an actual oil content. For instance, if such a method is to be applied in a supercritical refrigerating cycle where a refrigerant in a refrigerating machine is substantially in a supercritical state, a vapor phase state, or a gas-liquid double phase state, it is difficult to simply obtain the oil content by the above conventional method.

In other words, in the above supercritical state or the vapor phase state, compared to the liquid phase state, the electrostatic capacity of the refrigerant dramatically changes not only because of the temperature but also because of the pressure, this results in the need for an enormous amount of data that represents the relation between the electrostatic capacity and the oil content, which need to be prepared in advance. This data is difficult to compile and manage.

SUMMARY OF THE INVENTION

In view of the above problem, therefore, it is an object of the present invention to provide an oil content measuring device which is capable of easily measuring an oil content in a refrigerant even though the refrigerant is in a supercritical state or in a vapor phase state. Additionally, it is an object to provide a refrigeration system using such an oil content measuring device.

For solving the above problem, the following technical means are adopted in at least one embodiment of the present invention. According to a first aspect of the present invention, there is provided an oil content measuring device including an electrostatic capacity measuring means (200) for measuring an electrostatic capacity (C) of a refrigerant containing a refrigerating machine oil, a density measuring means (300) for measuring a density ($\varrho$) of at least one of the refrigerant and the refrigerating machine oil, a computing means (400) for computing correlation characteristics between the electrostatic capacity (C) and an oil content ($\chi$) using the density ($\varrho$) measured by the density measuring means (300), the oil content ($\chi$) representing a ratio of an amount of the refrigerating machine oil to an amount of the refrigerant containing the refrigerating machine oil, and an oil content determining means (500). The oil content determining means (500) for determining oil content ($\chi s$) from an electrostatic capacity (Cs) measured by the electrostatic capacity measuring means (200) using the correlation characteristics obtained by the computing means (400).

When the oil content measuring device is constructed as above, the electrostatic capacity (C) of the refrigerant can be calculated at the temperature and pressure used in the measurement by making use of the density ($\varrho$) of the refrigerant or the refrigerating machine oil even though the refrigerant in the refrigerating machine is in a supercritical state or in a vapor phase state. The electrostatic capacity of the refrigerant changes greatly depending on the changes in temperature and pressure, for example, as in the case of a supercritical refrigerating cycle, to determine the correlation characteristics between the electrostatic capacity (c) and the oil content ($\chi$) of the refrigerant. Consequently, it becomes possible to easily obtain the oil content ($\chi$) of the refrigerant without preparing an enormous amount of given data in advance.

Furthermore, it becomes possible to prevent the compressor (11) of the refrigeration system (10) from early damage before happens by periodically checking the oil content ($\chi$) of the refrigerant at the service store or the like.

Furthermore, in a vapor compression refrigerating cycle having a normal vapor phase state and a normal liquid phase state, a refrigerant in a stable liquid phase state is limited on the outflow side of a cooling body (12) having a supercooling function. In this case, the conventional measurement can be also allowed to obtain the oil content ($\chi$) of the refrigerant at such a position. However, the conventional measurement cannot be performed on both the discharge side and the suction side of the compressor (11) where the refrigerant is in a vapor phase state, so that it is hard to perform a proper measurement in the compressor (11) to obtain the oil content ($\chi$) of the refrigerant. According to the present invention, on the other hand, it is possible to perform a proper measurement on each of these sides.

According to a second aspect of the present invention, the computing means (400) performs a computation on the correlation characteristics between the electrostatic capacity (C) and the oil content ($\chi$) at temperature and pressure conditions at the time of the measurement by linear interpolation using a density ($\varrho r$) of the refrigerant on the basis of a plurality of correlation characteristics between the electrostatic capacity (C) and the oil content ($\chi$) previously prepared under a plurality of temperature and pressure conditions.

In this invention, the electrostatic capacity (C) of the refrigerant is linearly approximated based on the density ($\varrho r$) of the refrigerant, so that it becomes possible to precisely determine the correlation characteristics to be required in the measurement from the given correlation characteristics using the density ($\varrho r$) of the refrigerant.

According to a third aspect of the present invention, the computing means (400) performs a computation on the correlation characteristics between the electrostatic capacity (C) and the oil content ($\chi$) using an arithmetic expression previously defined such that the electrostatic capacity (C) is determined by the oil content ($\chi$), a density ($\varrho r$) of the refrigerant, and a density ($\varrho$oil) of the refrigerating machine oil.

In this invention, the assumption is made that the refrigerant and the refrigerating machine oil in a capacitor part (209) of the electrostatic capacity measuring means (200) are placed in series. Thus, the correlation characteristics between the electrostatic capacity (C) and the oil content ($\chi$) of the refrigerant are obtained using an arithmetic expression including the density ($\varrho r$) of the refrigerant and the density ($\varrho$oil) of the refrigerating machine oil. Consequently, it is possible to perform a computation on the above correlation characteristics using the above densities ($\varrho r$, $\varrho$oil) which can be easily detected even though there is no given data consisting of correlation characteristics.

According to a fourth aspect of the present invention, the density measuring means (300) includes temperature detecting means (301) for detecting a temperature of the refrigerant and a pressure detecting means (302) for detecting a pressure, and the density ($\varrho$) is calculated using detected values obtained by the temperature detecting means (301) and the pressure detecting means (302), respectively. Therefore, the density ($\varrho$) can be detected without requiring a complicated device and the oil content ($\chi$) can be obtained.

According to a fifth aspect of the present invention, the oil content ($\chi$) can be determined by replacing the electrostatic capacity (C) with a relative dielectric constant ($\epsilon$) divided by an electrostatic capacity (Co) in a vacuum. Therefore, the electrostatic capacity (C) can be treated as a nondimensional physical value ($\epsilon$), so that it can always be employed without wasting given data relating to the correlation characteristics even when the specifications of the electrostatic capacity measuring means (200) are changed.

According to a sixth aspect of the present invention, each of the electrostatic capacity (C) and the density ($\varrho$) is measured at a position in the vicinity of a suction side or a discharge side of a compressor (11) that compresses the refrigerant. Therefore, the oil content ($\chi$) in the vicinity of the compressor (11) itself can be known, so that one can make a precise and quick judgment whether the long-lasting durability of the compressor (11) is appropriate.

According to a seventh aspect of the present invention, a water repellent finishing is applied to surfaces of electrodes (207, 208) of the electrostatic capacity measuring means (200) when each of the electrostatic capacity (C) and the density ($\varrho$) is measured at a position in the vicinity of the suction side of the compressor (11). On the suction side of the compressor (11) where the refrigerant reaches a low temperature and a low pressure, the viscosity of the refrigerating machine oil increases and thus tends to adhere to the inside of the electrostatic capacity measuring means (200). According to the invention, it becomes possible to prevent the refrigerating machine oil from adhering to the inside of the electrostatic capacity measuring means (200), permitting precise measurement of the oil content ($\chi$) and also permitting a reliable circulation of the refrigerating machine oil in the compressor (11).

According to an eighth aspect of the present invention, a refrigeration system has an accumulator (18) for performing gas-liquid separation on the refrigerant, and an oil-returning flow path (19) for supplying a refrigerating machine oil in the separated liquid-phase refrigerant into a compressor (11) for compressing the refrigerant. The oil content measuring device (100) according to any one of the foregoing aspects of the invention is arranged in piping (21) through which the refrigerant flows. The amount of the refrigerating machine oil passing through the oil-returning flow path (19) varies depending on an oil content ($\chi$s) determined by the oil content measuring device (100). Therefore, the required refrigerating machine oil is supplied to the compressor (11) thereby increasing the durability of the compressor (11).

According to a ninth aspect of the present invention, each of electrodes (207, 208) of the electrostatic capacity measuring means (200) is shaped like a needle and is arranged in the piping (21) through which the refrigerant flows. Therefore, any container for housing the electrostatic capacity measuring means (200) can be eliminated, resulting in saved space and a cost reduction. In addition, since each of the electrodes (207, 208) is shaped like a needle, the electrodes are highly flexible. Additionally, arrangement is possible on a portion where the piping (21) is bent, which results in an excellent mounting ability.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

PREFERRED EMBODIMENTS OF THE INVENTION

The following description of the preferred embodiments is merely exemplary in nature and is in no way intended to limit the invention, its application, or uses.

[First Embodiment]

Figure 1:
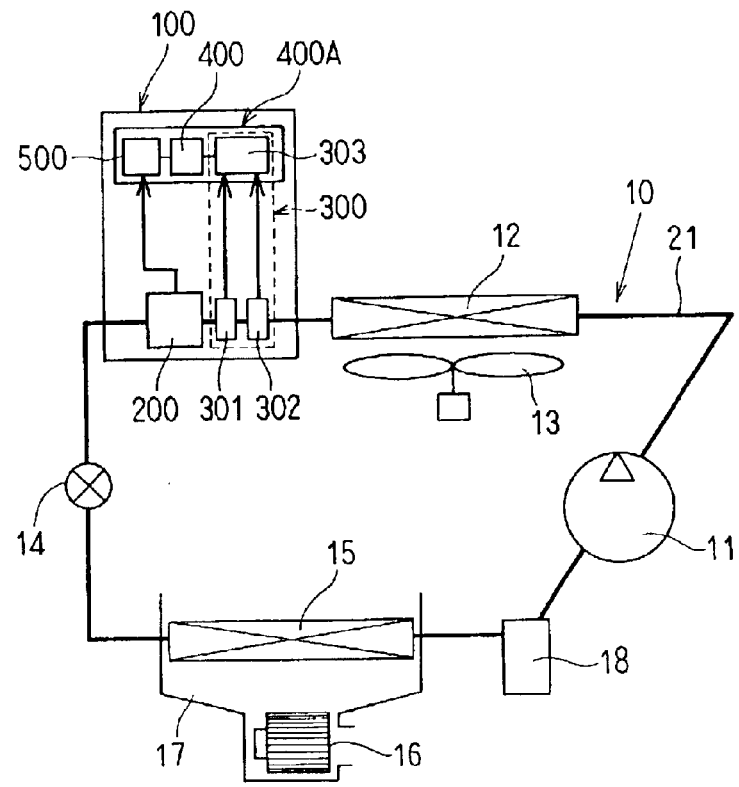
FIG. 1 is a schematic view that illustrates the overall view of the configuration of a first embodiment of the present invention.

A first embodiment of the present invention is illustrated in FIGS. 1 to 10. FIG. 1 illustrates the overall view of the embodiment. In this embodiment, an oil content measuring device is constructed such that it is capable of measuring the oil content $\chi$ in a refrigerant of a refrigeration system 10.

The refrigeration system 10 constitutes a well-known refrigerating cycle and includes: a compressor 11 for compressing a refrigerant to a high temperature and a high pressure; a cooling body 12 for cooling the compressed refrigerant; an expansion valve 14 for performing an adiabatic expansion of the cooled refrigerant; an evaporator 15 for vaporizing the expanded refrigerant by evaporation; and an accumulator 18 for performing a gas-liquid separation on the refrigerant. These structural components are sequentially connected to each other through piping 21. In the cooling body 12, there is provided an air blower 13 for facilitating heat exchange in the cooling of the refrigerant. Also, the evaporator 15 is housed in an air-conditioning case 17, where the air blowing from the air blower 16 is cooled by an evaporation latent heat in the evaporation of the refrigerant.

In this embodiment, the refrigerant used in the refrigeration system 10 is $CO_2$, which is provided to act as the so-called supercritical refrigerating cycle in which higher pressures caused by the compressor 11 exceed a critical pressure. In addition, the compressor 11 contains a refrigerating machine oil (hereinafter, also referred to as a lubricating oil) for facilitating an actuation of the compressor 11 itself. The lubricating oil flows together with the refrigerant through the piping 21 by actuating the compressor 11.

In this embodiment, an oil content measuring device 100 is arranged between the cooling body 12 and the expansion valve 14 in the refrigeration system 10, so that it becomes possible to measure the oil content $\chi$. The oil content measuring device 100 includes an electrostatic capacity measuring device 200, a density measuring device 300, a computing device 400, and an oil content determining device 500.

Figure 2:
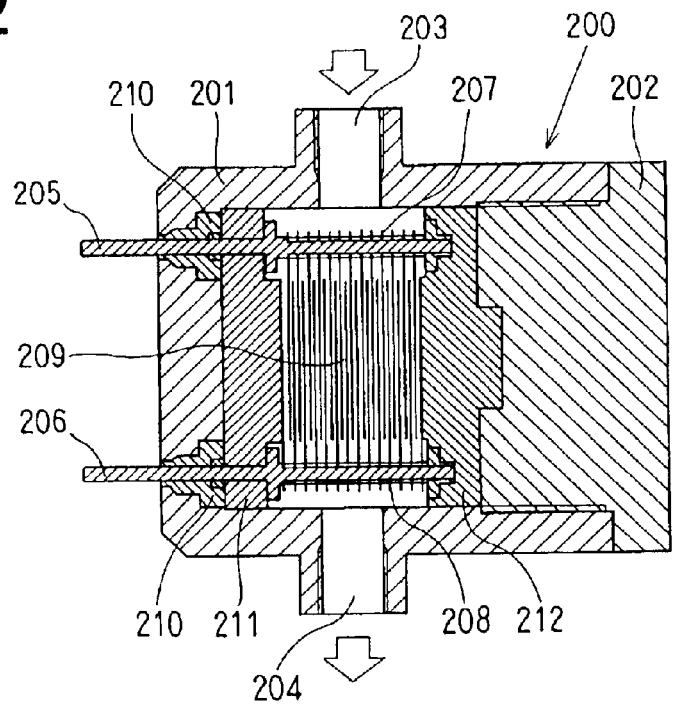
FIG. 2 is a cross-sectional view that illustrates an electrostatic capacity measuring device.

The electrostatic capacity measuring device 200 is a means for measuring an electrostatic capacity. As shown in FIG. 2, the device 200 has body parts 201 and 202 which constitute a pressure tight case, and a capacitor part 209 installed in the pressure tight case of the body parts 201 and 202. In the inner space of the case, terminal rods 205 and 206 are oppositely provided. Pluralities of electrodes 207 and electrodes 208 are respectively fixed on the terminal rods 205 and 206 by soldering such that the electrodes 207 and 208 are alternately aligned and extend from the opposite sides without being in contact with each other and ultimately form the capacitor part 209. Then, the capacitor part 209 is surrounded by the insulating bodies 210, 211 and 212 so as to be insulated from the exterior body parts 201, 202. As shown in the figure, the body part 201 has an inlet portion 203 and an outlet portion 204, so that the refrigerant in the refrigeration system 10 can be circulated between the electrodes 207 and 208 in the capacitor part 209.

Furthermore, positive and negative charges are applied on the terminal rods 205 and 206, respectively, so that it becomes possible to measure an electrostatic capacity C of the refrigerant (one containing lubricating oil) circulating through the capacitor part 209. In this embodiment, here, a four-terminal method is employed for improving the accuracy of measuring the electrostatic capacity C.

The density measuring device 300 is a means for measuring the density of the refrigerant and includes a temperature sensor 301 as a temperature detecting means, a pressure sensor 302 as pressure detecting means, and a density computing part 303. Each of the temperature sensor 301 and the pressure sensor 302 are arranged on the piping 21 so as to be located in the vicinity of the electrostatic capacity measuring device 200. The density computing part 303 receives a signal with respect to a temperature of the refrigerant containing the lubricating oil from the temperature sensor 301 and a pressure-detecting signal from the pressure sensor 302. The density computing part 303 is then allowed to determine the density $\varrho r$ of the refrigerant in the measurement on the basis of the above input signals together with a previously stored density characteristic line diagram (the density values with respect to temperature and pressure).

The computing device 400 constitutes a computing means and has the ability of performing a computation on the correlation characteristics between the electrostatic capacity C of the refrigerant containing the lubricating oil and the oil content $\chi$ of the refrigerant. The oil content $\chi$ represents the ratio of the lubricating oil in the refrigerant. Here, a plurality of correlation characteristics between the electrostatic capacity C and the oil content $\chi$ are prepared in advance using a plurality of temperatures and pressures as their respective parameters and then stored as given data in the computing device 400. Then, the computing device 400 performs a computation on the correlation characteristics in the measurement from the given data employing linear interpolation using the density er of the refrigerant obtained by the density measuring device 300. The details thereof will be described later.

In this embodiment, the definition of the above oil content $\chi$ can be represented by the following formula (1).

Oil content$\chi$=(mass of lubricating oil)/((mass of refrigerant)+(mass of lubricating oil)) (1)

Here, mass of each of the lubricating oil and the refrigerant is on a per unit-volume basis.

An oil content determining device 500 is a means for determining the oil content of a refrigerant. This device 500 has a computing function for obtaining an oil content λs in the measurement on the basis of the electrostatic capacity Cs measured by the above electrostatic capacity measuring device 200 from correlation characteristics between an electrostatic capacity C, which is obtained by a computation with linear interpolation in the above computing device 400, and an oil content $\chi$. The above density computing part 303, computing device 400, and oil content determining device 500 are assembled together to integrally constitute a computing unit 400A.

Hereinafter, the operation of the oil content measuring device as constructed above will be described with particular emphasis on the process for computing the correlation characteristics between the electrostatic capacity C and the oil content $\chi$ in the computing device 400.

As the refrigeration system 10 is actuated, the refrigerant and the lubricating oil circulate through the piping 21. At first, the electrostatic capacity measuring device 200 determines the electrostatic capacity Cs of the refrigerant containing the lubricating oil at the time of actuating the refrigeration system 10, while determining temperature Ts and pressure Ps at the time of such an actuation by both sensors 301, 302 in the density measuring device 300. Subsequently, the density $\varrho$rs of the refrigerant is calculated in the density computing part 303 on the basis of the measured temperature Ts and pressure Ps.

In the computing unit 400, correlation characteristics at temperature Ts and pressure Ps at the time of measuring are estimated on the basis of correlation characteristics between the electrostatic capacity C and the oil content $\chi$ using a plurality of given data prepared in advance, including temperatures and pressures. For such an estimation, furthermore, a linear interpolation is performed using the density $\varrho$r of the refrigerant (i.e., $\varrho$rs in the measurement and randomly selected $\varrho$r1 to $\varrho$r6).

Figure 3:
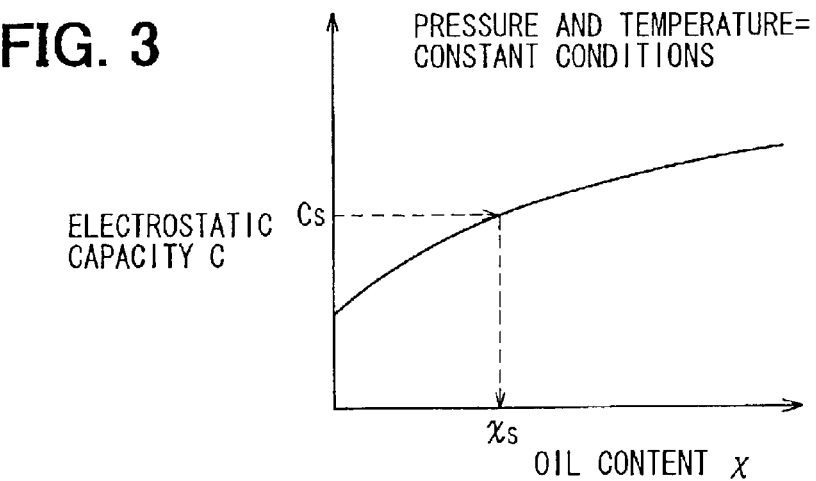
FIG. 3 is a correlation characteristic diagram between the electrostatic capacity C and the oil content $\chi$.

Here, for a clearer explanation, the linear interpolation will be described after additional explanations are provided for the correlation characteristics between the electrostatic capacity C, the oil content $\chi$, and additional data. The phrase "the correlation characteristics between the electrostatic capacity C and the oil content $\chi$" represents the relationship between the electrostatic capacity C and the oil content $\chi$, which is established as shown in FIG. 3. The refrigerant (in the embodiment, $CO_2$) and the lubricating oil (in the embodiment, PAG) have their own dielectric constants and are different from each other. In other words, the dielectric constant of the lubricating oil is higher than that of the refrigerant. Therefore, the dielectric constant of the refrigerant containing the lubricating oil depends on their mixing ratio. That is, the dielectric constant of the refrigerant containing the lubricating oil increases as the oil content $\chi$ thereof increases.

In general, the electrostatic capacity C is proportional to the dielectric constant $\epsilon$ as expressed by the following equation:

$$C = \epsilon \cdot \epsilon o \cdot S / do$$

wherein "C" denotes the electrostatic capacity, "$\epsilon$" denotes a dielectric constant, "$\epsilon o$" denotes a dielectric constant in a vacuum, "S" denotes the area of an electrode portion of the capacitor part 209 used in the measurement of the electrostatic capacity C, and "do" denotes the distance between the electrodes in the electrode portion of the capacitor part 209.

As is evident from the above equation, therefore, that the electrostatic capacity C has a positive correlation with the oil content $\chi$. Therefore, the present invention is based on obtaining the oil content $\chi$ from the measured electrostatic capacity Cs by utilizing the correlation characteristics between the electrostatic capacity C and the oil content $\chi$.

If the refrigerant is in a liquid phase state, each of the temperature and the pressure can be uniquely defined. For instance, if the temperature is used as one of the parameters and the correlation characteristics including the temperature condition in the measurement is prepared in advance, the oil content $\chi$ can be measured as described in the above description of the prior art.

Figure 4:
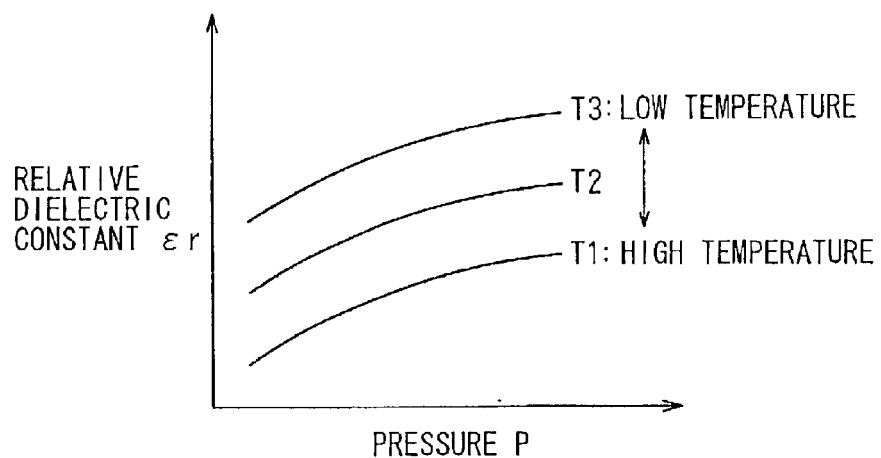
FIG. 4 is a graph representing the relative dielectric constant of the refrigerant which varies with temperature and pressure.
Figure 5:
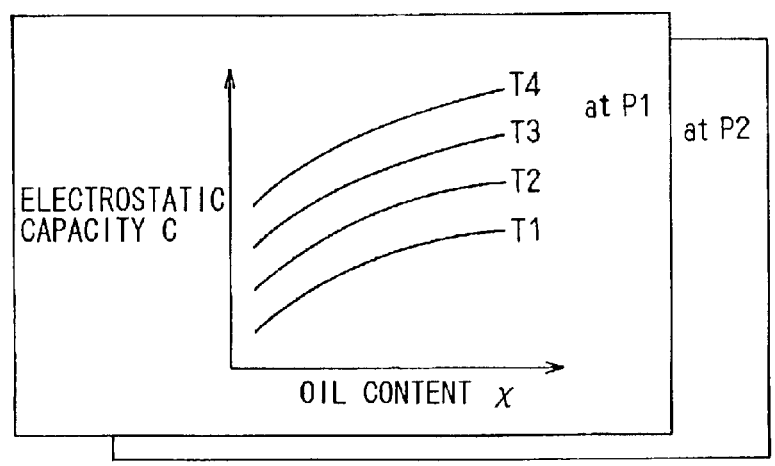
FIG. 5 is a schematic view that illustrates an image of given data at temperatures T1–T4 and pressures P1 and P2.

However, if the refrigerant is in a supercritical state or in a vapor phase state, as shown in FIG. 4, the relative dielectric constant $\epsilon r$ may be substantially varied as a result of the variations in temperature even though the pressure is being kept at a constant. In order to obtain a correct oil content $\chi$, there is a need to prepare a large number of correlation characteristics using parameters of different temperatures and pressures. In this embodiment, however, the calculation of the oil content $\chi$ can be attained without depending on a large number of correlation characteristics. That is, the present embodiment is based on correlation characteristics with permanent reference values of parameters which can be prepared within the temperatures and pressures to possibly be used in the actual measurement (here, as a minimum condition, two pressure levels and four temperature levels are used) to perform a liner interpolation for obtaining the oil content $\chi$. The correlation characteristics as shown in FIG. 5 are provided as given data to be used in the present embodiment and are stored in the computing device 400 in advance.

Considering the above facts, we will describe the linear interpolation for determining the correlation characteristics between the electrostatic capacity C and the oil content $\chi$ in the measurement. The "linear interpolation" used herein is designed for estimating a correlation characteristic in the measurement, which can be expected to be present between two already-known correlation characteristics, utilizing the ratio of refrigerant densities $\varrho$r under temperature and pressure conditions of the respective correlation characteristics. In this case, attention is paid to the fact that the relative dielectric constant $\varrho$r of the refrigerant can be linearly approximated based on the density $\varrho$r thereof.

From the Clarsius-Mosotti equations as shown in the following equations (2) and (3), the relative dielectric constant $\epsilon r$ of the refrigerant can be linearly approximated based on the density $\varrho$r of the refrigerant.

$$\epsilon r = (D + 2\varrho r)/(D - \varrho r) \qquad (2)$$

$$D = 3 \cdot \epsilon o \cdot M / \alpha \cdot N \qquad (3)$$

wherein "$\epsilon r$" denotes a relative dielectric constant of the refrigerant; "$\varrho r$" denotes the density of the refrigerant (kg/m$^2$); "$\epsilon o$" denotes a dielectric constant in vacuum (F/m); "M" denotes a molecular weight (kg/mol); "$\alpha$" denotes a polarizability (Fm$^2$); and "N" denotes Avogadro's number (1/mol).

From the above equations (2) and (3), when the relative dielectric constant $\epsilon r$ of the refrigerant is differentiated with the density $\varrho r$ of the refrigerant, the resulting value is substantially constant as represented by equation (4) below.

$$\partial \epsilon r / \partial \varrho r = 3D/(D - \rho r)^2 = 3 \times 6580/(6580 - \varrho r)^2 \qquad (4)$$

constant ($\varrho r << 6580$)

Figure 6:
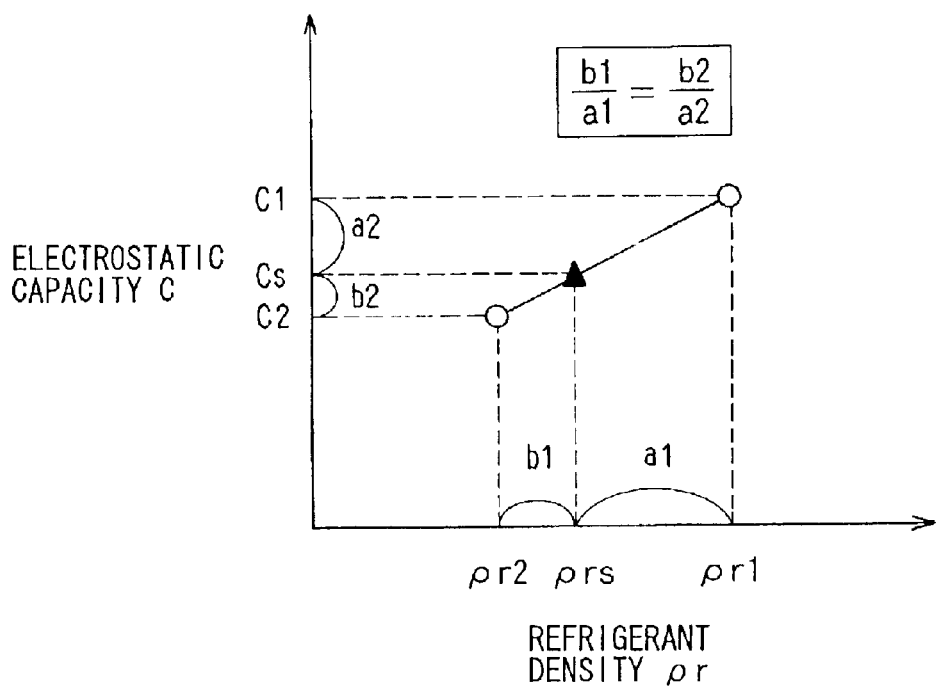
FIG. 6 is a graph representing a linear approximation of electrostatic capacity with the refrigerant density.

Therefore, it is considered that the relative dielectric constant $\epsilon r$ of the refrigerant may be linearly approximated based on the density $\varrho r$ of the refrigerant. For this reason, as shown in FIG. 6, it is considered that the electrostatic capacity C of the refrigerant in proportion to the relative dielectric constant $\varepsilon r$ of the refrigerant can be linearly approximated based on the density $\varrho r$ of the refrigerant. Points C1 and C2 are also shown.

Figure 7:
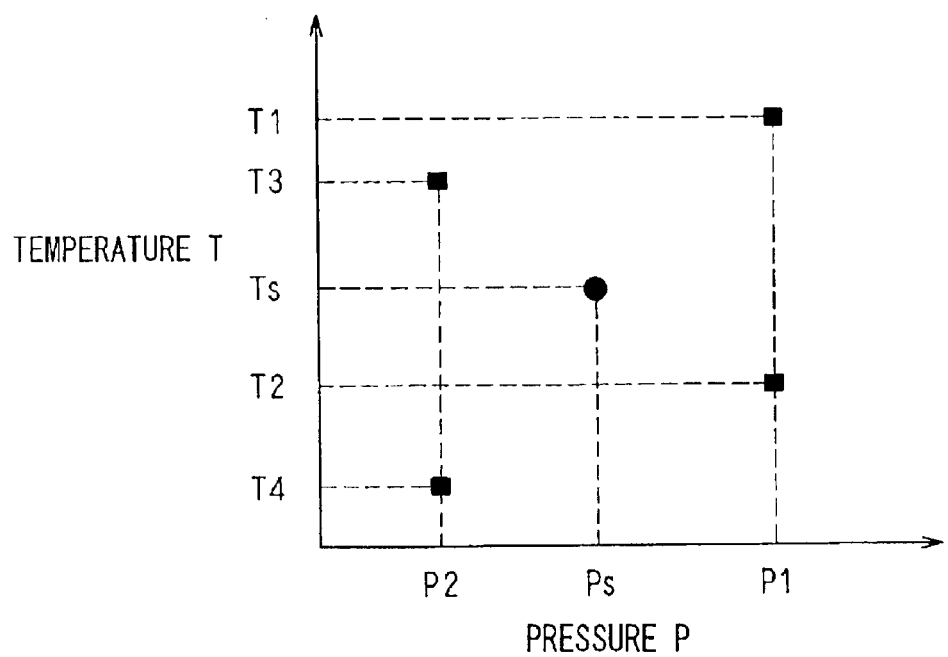
FIG. 7 is a graph representing the coordinates of pressure and temperature selected for linear interpolation.

Depending on the idea described above, the essential point of the linear interpolation will be described below. As described above, first, the electrostatic capacity Cs, the temperature Ts, the pressure Ps, and the refrigerant density $\varrho r$ are measured using the respective measuring devices 200 and 300. Then, four correlation characteristics having the temperature and pressure conditions proximate to the above temperature Ts and the pressure Ps are provided from the given data. That is, as shown in FIG. 7, P1 and P2 are selected as the pressures for the selected correlation characteristics, where they may be in the range of P2≦Ps<P1. In addition, for the pressure P1, the correlation characteristics with temperatures T1 and T2 (T2≦Ts<T1) are selected. On the other hand, for the pressure P2, the correlation characteristics with temperatures T3 and T4 (T4≦Ts<T3) are selected.

Subsequently, from each temperature and pressure condition of the four selected correlation characteristics, the densities $\varrho r1$ to $\varrho r4$ of the refrigerant are calculated by the density measuring device 300. Furthermore, the density $\varrho r5$ of the refrigerant at higher pressure P1 and measuring temperature Ts and the density $\varrho r6$ of the refrigerant at lower pressure P2 and measuring temperature Ts are additionally calculated.

Figure 8:
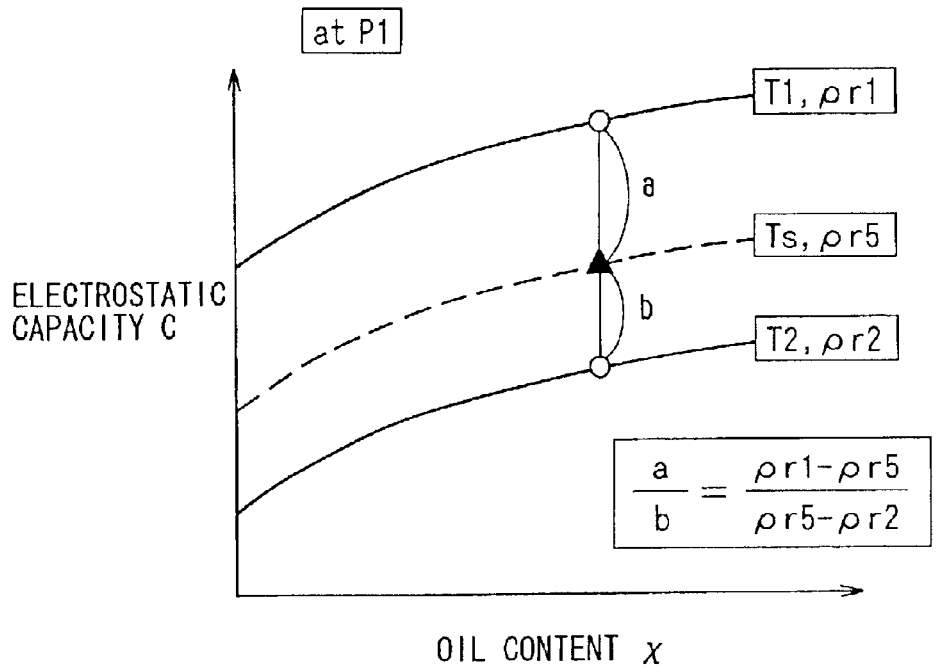
FIG. 8 is a graph representing a linear interpolation between the temperatures T1 and T2 at pressure P1.
Figure 9:
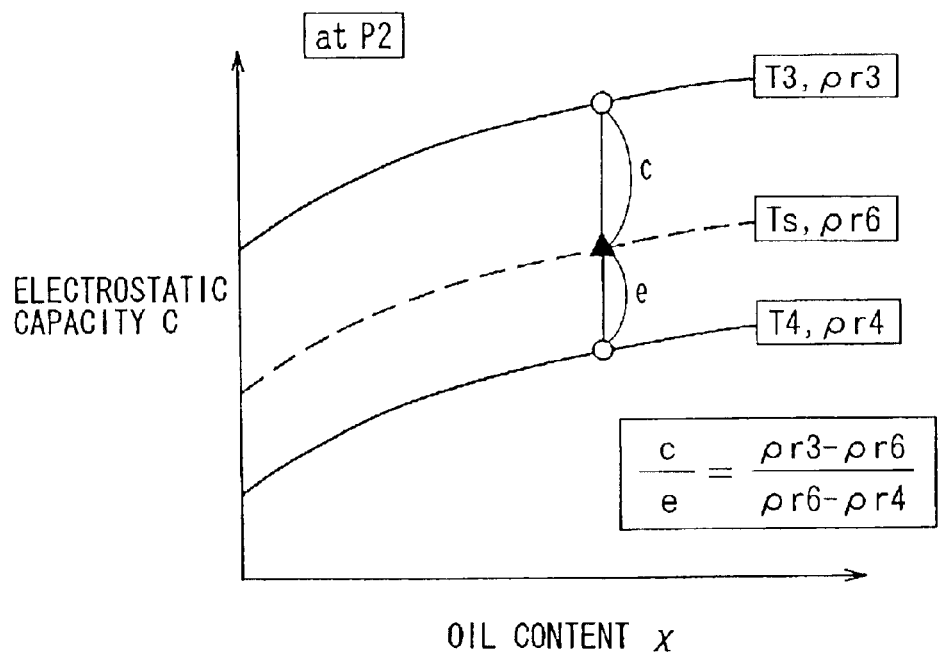
FIG. 9 is a graph representing a linear interpolation between the temperatures T3 and T4 at pressure P2.

As shown in FIG. 8, furthermore, correlation characteristics at pressure P1 and measuring temperature Ts are estimated by linear interpolation using the densities $\varrho r1$, $\varrho r2$, and $\varrho r5$ of the refrigerant. Temperatures T1 and T2 are also shown on the graph. As described above, such an estimation can be allowed by a proportional distribution between two known correlation characteristics as the ratio of a/b=($\varrho r1-\varrho r5$)/($\varrho r5-\varrho r2$) because the electrostatic characteristic capacity C can be linearly approximated based on the refrigerant density $\varrho r$. Likewise, as shown in FIG. 9, correlation characteristics at pressure P2 and measuring temperature Ts are estimated by linear interpolation using the densities $\varrho r3$, $\varrho r4$, and $\varrho r6$ of the refrigerant (here, a proportional distribution is performed so as to be a ratio of c/e=(($\varrho r3-\varrho r6$)/($\varrho r6-\varrho r4$)). Temperatures T3 and T4 are also shown. Finally, the interpolation is performed using the refrigerant densities $\varrho r5$ and $\varrho r6$ obtained in FIGS. 8 and 9 and the initially measured refrigerant density $\varrho rs$ to estimate the correlation characteristics at pressure Ps and temperature Ts as shown in FIG. 10 (here, a proportional distribution is performed so as to be a ratio of f/g=(($\varrho r5-\varrho rs$)/($\varrho rs-\varrho r6$)).

Figure 10:
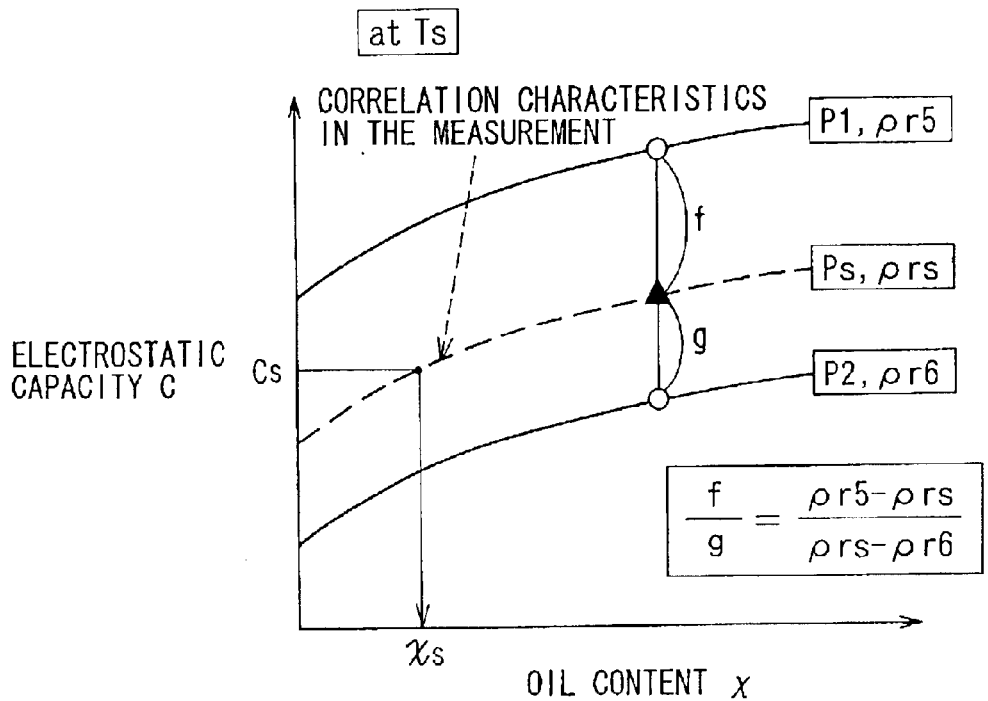
FIG. 10 is a graph representing a linear interpolation between the pressures P1 and P2 at temperature Ts.

The correlation characteristic shown in FIG. 10 and obtained by linear interpolation described above are to be provided as those in the measurement, so that the oil content $\chi s$ corresponding to the electrostatic capacity Cs measured in the oil content determining device 500 use such correlation characteristics. Therefore, like the present embodiment, the correlation characteristics with the oil content $\chi$ can be determined using the density $\varrho r$ of the refrigerant even in a supercritical state or in a vapor phase state, where the electrostatic capacity C of the refrigerant in the refrigerating machine can be substantially varied depending on temperature and pressure as in the supercritical refrigerating cycle. Thus, the oil content $\chi$ can be easily obtained without preparing a large amount of given data in advance.

Therefore, in the present invention, it is found that the electrostatic capacity C of the refrigerant can be linearly approximated based on the density $\varrho r$ of the refrigerant. The correlation characteristics to be required in the measurement can be precisely obtained from the linear interpolation of the known correlation characteristics using the density $\varrho r$ of the refrigerant. Therefore, the oil content $\chi$ can be easily obtained without preparing a large quantity of data in advance. Thus, early damage of the compressor 11 in the refrigeration system 10 can be prevented by periodically checking the oil content $\chi$ using the oil content measuring device 100 in a service shop, or the like, or using the device 100 mounted on the vehicle.

In this embodiment, the density $\varrho r$ of the refrigerant is calculated based on a value detected by the temperature sensor 301 and the pressure sensor 302, so that there is no need to use a complicated device to detect the density $\varrho r$, thereby permitting the determination of the oil content $\chi$.

Furthermore, in the case of a vapor-compression type refrigerating cycle including a typical vapor state and a typical liquid phase state, the refrigerant in a stable liquid phase state is localized only on the outflow side of the cooling body 12 having an over-cooling function. The conventional measurement of the oil content $\chi$ may be possible on this portion. However, the conventional measurement cannot be performed on the discharge side or the suction side of the compressor 11 which may be in a vapor phase state, resulting in a poor measurement of the oil content $\chi$. In this embodiment, on the other hand, the oil content $\chi$ can be precisely measured.

In this embodiment, furthermore, the refrigeration system 10 uses $CO_2$ as its refrigerant and a supercritical refrigerating cycle to be actuated at a critical pressure or more. The present invention is not limited to such a configuration of the refrigeration system 10. Alternatively, the present embodiment may be applied on a typical refrigeration system in which Freon or the like is used as a refrigerant.

[Second Embodiment]

Figure 11:
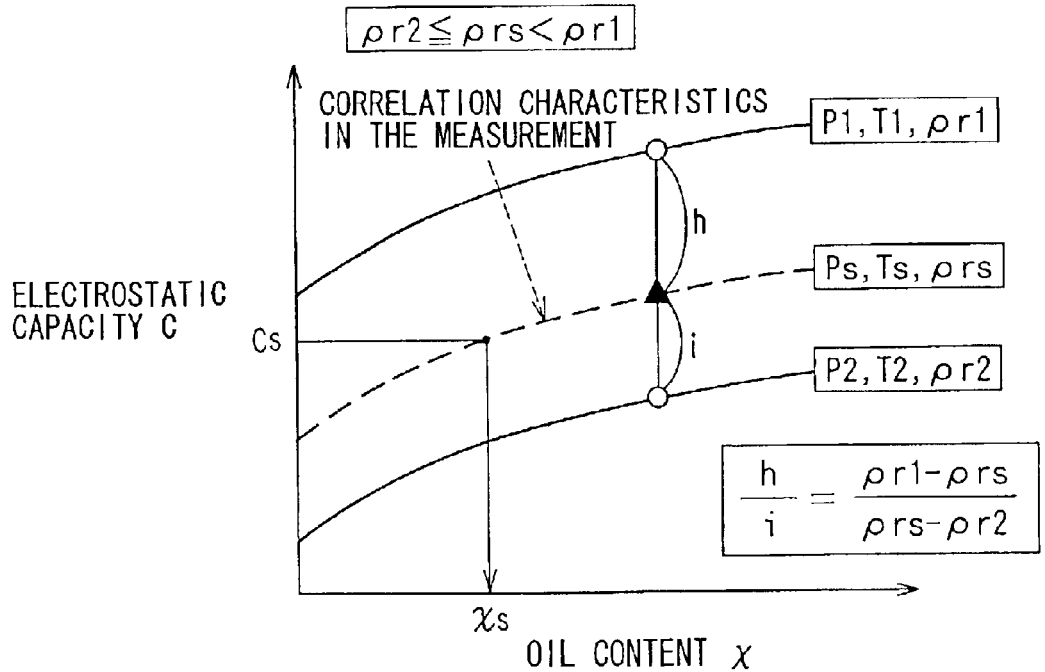
FIG. 11 is a graph representing a linear interpolation between the refrigerant densities $\varrho r1$ and $\varrho r2$ in a second embodiment of the present invention.

A second embodiment of the present invention is illustrated in FIG. 11, which shows the basic procedures for obtaining correlation characteristics between the electrostatic capacity C and the oil content $\chi$ of a refrigerant in the measurement by linear interpolation. In this embodiment, compared with the first embodiment, there is provided an alternative process for calculating the correlation characteristics in the measurement in the computing device 400.

The principal configuration of the present embodiment is the same as that of the first embodiment, except that given data are selected on the basis of the density $\varrho r$ of the refrigerant which was previously calculated with respect to temperature T and pressure P in the given data.

First, the density $\varrho rs$ of the refrigerant in the measurement is calculated in the density measuring device 300. Then, two correlation characteristics proximate to the obtained density $\varrho rs$ of the refrigerant are selected from those in the given data. That is, one correlation characteristic under the conditions of refrigerant density $\varrho r1$, pressure P1, and temperature T1, and the other correlation characteristics under the conditions of refrigerant density $\varrho r2$, pressure P2, and temperature T2 are selected so as to be $\varrho r2 \leq \varrho rs < \varrho r1$.

Then, as shown in FIG. 11, just as in the case with the first embodiment, the interpolation is performed using the refrigerant densities $\varrho r1$, $\varrho r2$, and the initially measured refrigerant density $\varrho rs$ to estimate the correlation characteristics at pressure Ps and temperature Ts (here, a proportional distribution is performed so as to be a ratio of h/i=(($\varrho r1-\varrho rs$)/($\varrho rs-\varrho r2$)). Thereby, the oil content $\chi$ can be calculated with respect to the electrostatic capacity Cs.

In the above first embodiment, the correlation characteristics in the measurement are obtained by selecting four correlation characteristics from the given data and performing linear interpolations three times. In the second embodiment, on the other hand, two correlation characteristics are selected from the given data on the basis of the refrigerant density $\varrho r$, and the correlation characteristics in the measurement can be calculated by a single linear interpolation. Therefore, the second embodiment is allowed to calculate the oil content $\chi$ more easily.

[Third Embodiment]

In a third embodiment, compared with the above first embodiment, the oil content $\chi$ is obtained using the relative dielectric constant $\epsilon$ (i.e., the relative dielectric constant of a refrigerant containing a lubricating oil) instead of the electrostatic capacity C.

The third embodiment has the same configuration as that of the above first embodiment, except that the electrostatic capacity measuring device 200 has an additional computing function in which the measured electrostatic capacity C is converted into the relative dielectric constant C on the basis of equation (5), set forth below. In this embodiment, furthermore, a relative dielectric constant in the measurement to be obtained by the electrostatic capacity measuring device 200 will be represented as "$\epsilon s$."

$$\epsilon = (C-SC)/(Co-SC) \tag{5}$$

wherein "$\epsilon$" denotes a relative dielectric constant of the refrigerant containing the lubricating oil; "C" denotes the measured electrostatic capacity of the refrigerant; "SC" denotes a stray capacitance; and "Co" denotes the electrostatic capacity in vacuum. The correlation characteristics as given data to be stored in the computing device 400 is to be the relationship between the above relative dielectric constant $\epsilon$ and the oil content $\chi$.

For measuring the oil content $\chi$, first the electrostatic capacity Cs is measured and is then converted into a relative dielectric constant $\epsilon s$, followed by performing the same steps as those of the first embodiment to calculate the correlation characteristics (i.e., the relationship between the relative dielectric constant $\epsilon s$ and the oil content $\chi$) from the linear interpolation to obtain the oil content $\chi s$ with respect to the relative dielectric constant $\epsilon s$. Furthermore, the reason why the linear interpolation becomes possible in the correlation characteristics between the relative dielectric constant $\epsilon$ and oil content $\chi$ can be clarified by the description related to equations (2) to (4) in the above first embodiment.

In this embodiment, therefore, the electrostatic capacity C can be handled as a physical value ($\epsilon$) in a dimensionless form. It becomes possible to always effectively use the given data for the correlation characteristics without wasting any given data even though the specifications of the electrostatic capacity measuring device 200 are altered (the capacitor part 209).

[Fourth Embodiment]

In a fourth embodiment of the present invention, compared with each of the first to third embodiments, there is no need to provide the correlation characteristics as given data. In this embodiment, an arithmetic expression is provided in advance such that the electrostatic capacity C is to be determined by the oil content $\chi$ and the refrigerator density $\varrho r$ and the lubricating oil density $\varrho oil$, which can be measured using the density measuring device 300, followed by obtaining the oil content $\chi$ after the calculation of correlation characteristics.

The basic configuration of the fourth embodiment is the same as that of the above first embodiment, except that the lubricating oil density $\varrho oil$ can be calculated simultaneously with the calculation of the refrigerant density $\varrho r$ in the density measuring device 300. In this embodiment, furthermore, an arithmetic expression of correlation characteristics is previously stored in the computing device 400, so that the correlation characteristics can be obtained using the electrostatic capacity C to be measured and both densities $\varrho r$ and $\varrho oil$. An idea for setting the arithmetic expression of correlation characteristics will be described below with reference to FIGS. 12A and 12B.

Figure 12A:
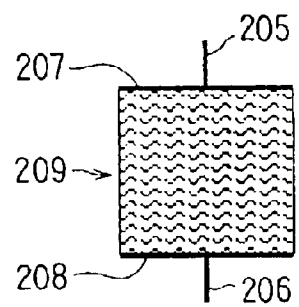
FIG. 12A is a schematic view illustrating a capacitor part in a state of mixing the refrigerant with the lubricating oil according to a fourth embodiment of the present invention.
Figure 12B:
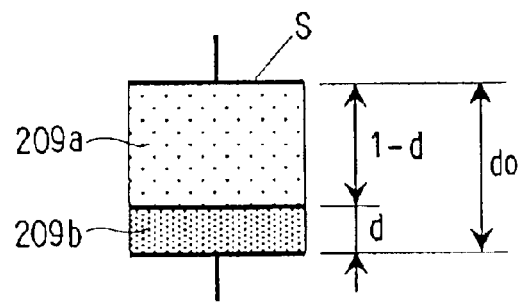
FIG. 12B is a schematic view illustrating the refrigerant and the lubricating oil arranged in series according to a fourth embodiment of the present invention.

First, we assume a model of the capacitor part 209 in the electrostatic capacity measuring device 200. That is, in actuality, the refrigerant and the lubricating oil are in a mixed state and the mixture thereof circulates through the capacitor part 209 as shown in FIG. 12A. In this embodiment, on the other hand, it can be replaced with a model shown in FIG. 12B, assuming that the capacitor part 209a filled with the refrigerant and the capacitor part 209b filled with the lubricating oil, are connected to each other in series.

Based on such a model, the arithmetic expression of the correlation characteristics can be derived as follows. The electrostatic capacity C of the whole capacitor part 209 can be expressed by the following equation (6) with the electrostatic capacity Cr of the refrigerant in the capacitor part 209a and the electrostatic capacity Coil of the lubricating oil in the capacitor part 209b.

$$1/C = 1/Cr + 1/Coil \tag{6}$$

The electrostatic capacity Co in vacuum can be expressed by the equation (7). The electrostatic capacity Cr of the refrigerant and the electrostatic capacity Coil of the lubricating oil can be expressed by the equations (8) and (9) using the equation (7), respectively.

$$Co = \epsilon_0 \cdot S/do \tag{7}$$

wherein "$\epsilon 0$" denotes a dielectric constant in vacuum (F/m); "S" denotes an area of the capacitor part (m$^2$); and "do" denotes a distance between the capacitor parts (m).

$$Cr = \epsilon r \cdot \epsilon_0 \cdot S/\{(1-d)do\} = \epsilon r \, Co/(1-d) \tag{8}$$

wherein "$\epsilon r$" denotes a relative dielectric constant of the refrigerant; and "d" denotes a volume ratio occupied by the lubricating oil.

$$Coil = \epsilon oil \cdot \epsilon_0 \cdot S/(d \cdot do) = \epsilon oil \cdot Co/d \tag{9}$$

wherein "$\epsilon oil$" denotes a relative dielectric constant of the lubricating oil.

Then, the following equation (10) can be obtained by substitutions of the equations (8) and (9) into the equation (6).

$$C = \epsilon r \cdot \epsilon oil \cdot Co/\{\epsilon r \, d + \epsilon oil(1-d)\} \tag{10}$$

Furthermore, the volume ratio d of the lubricating oil occupied in the refrigerant can be expressed as the following equation (11) as a parameter to be defined by the oil content $\chi$, the refrigerant density $\varrho r$, and the lubricating oil density $\varrho oil$.

$$d = \chi/\{\chi + (100-\chi) \cdot \varrho oil/\varrho r\} \tag{11}$$

In the above equation (10), the relative dielectric constant $\epsilon r$ of the refrigerant can be calculated from the equations (2) and (3) (i.e., the Clarsius-Mosotti equations described in the first embodiment) using the refrigerant density $\varrho r$. In addition, the relative dielectric constant $\epsilon oil$ of the lubricating oil can be calculated from equation (12) as a function of only temperature T because of the lubricating oil in a liquid phase state.

$$\epsilon \text{oil} = 5.60 - 0.01 \cdot T \quad (12)$$

Thus, the correlation between the electrostatic capacity C and the oil content χ can be obtained from the equations (10) and (11) using the refrigerant density ϱr and the lubricating oil density ϱoil. The equations (10) and (11) may be previously stored in the computing device 400 as the arithmetic expressions for correlation characteristics. In addition, the equations (2), (3), (7), and (12) which can be required in the computation are also stored together in the computing device 400.

Hereinafter, we will describe the method for measuring the oil content χ using the above arithmetic expressions of correlation characteristics. First, the electrostatic capacity Cs is obtained by the electrostatic capacity measuring device 200, and the refrigerant density ϱrs and the lubricating oil density ϱoils at measured pressure Ps and measured temperature Ts are then obtained by the density measuring device 300.

Next, in the computing device 400, the above refrigerant density ϱrs and the lubricating oil density ϱoils are used for calculating the volume ratio d of the lubricating oil occupied in the refrigerant using the equation (11) with any oil content χ. Subsequently, the relative dielectric constant εr of the refrigerant and the relative dielectric constant εoil of the lubricating oil are calculated using the equations (2), (3), and (12), while the electrostatic capacity Co in vacuum is calculated using the equation (7).

The volume ratio d of the lubricating oil occupied in the refrigerant, the relative dielectric constant εr of the refrigerant, the relative dielectric constant εoil of the lubricating oil, and the electrostatic capacity Co in vacuum are substituted into equation 10 to calculate an electrostatic capacity C at any oil content χ. Then, the above calculation is repeated while changing the oil content χ in an arbitrary manner, resulting in the correlation characteristics between the electrostatic capacity C and the oil content χ. An oil content χ corresponding to the initially measured electrostatic capacity Cs is measured, thereby determining the oil content χs to be measured.

According to the present embodiment, therefore, even if there is no given data for the correlation characteristics, the correlation characteristics between the electrostatic capacity C and the oil content χ from the refrigerant density ϱr and the lubricating oil density ϱoil are easily determined.

[Fifth Embodiment]

Figure 13:
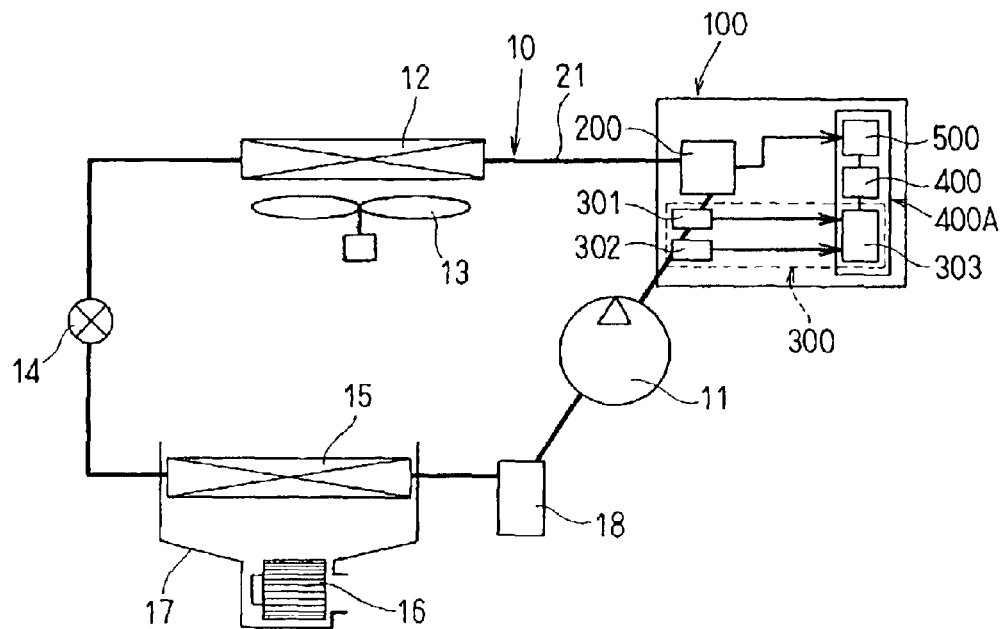
FIG. 13 is a schematic view that illustrates an overall view of a first variation of a fifth embodiment of the invention.
Figure 14:
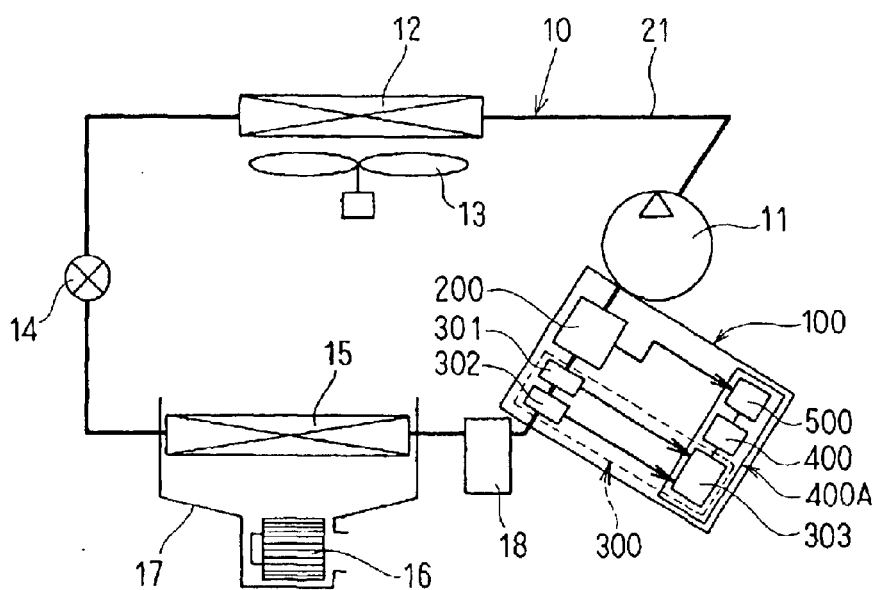
FIG. 14 is a schematic view that illustrates an overall view of a second variation of the fifth embodiment of the invention.

FIG. 13 and FIG. 14 illustrate a fifth embodiment of the present invention. In this embodiment, a position where the oil content measuring device 100 is installed is changed from one defined in the first embodiment.

The basic configuration of the fifth embodiment is the same as that of the first embodiment, except that the oil content measuring device 100 is placed between the compressor 11 and the cooling body 12 so as to be located in the vicinity of the discharge side of the compressor 11 in the refrigeration system 10 as shown in FIG. 13, or except that the oil content measuring device 100 is placed between the compressor 11 and the accumulator 18 so as to be located in the vicinity of the suction side of the compressor 11 as shown in FIG. 14.

In the fifth embodiment, therefore, the oil content χ can be obtained in the vicinity of the compressor 11, so that it becomes possible, in a correct and quick manner, to make a judgment whether the oil content is at a level that promotes the long-lasting durability of the compressor 11.

If the oil content measuring device 100 is arranged in the vicinity of the suction side of the compressor to measure the oil content χ, it is preferable to make a water repellent finish on the surface of each of the electrodes 207 and 208 of the electrostatic capacity measuring device 200. Therefore, in the fifth embodiment, it becomes possible to prevent the lubricating oil from sticking to the inside of the capacity measuring device 200, especially to the electrodes 207 and 208 as the viscosity of lubricating oil increases on the suction side where the refrigerant is at lower temperature and lower pressure. Thus, the oil content χ can be precisely calculated and the lubricating oil can be circulated through the compressor 11.

[Sixth Embodiment]

Figure 15:
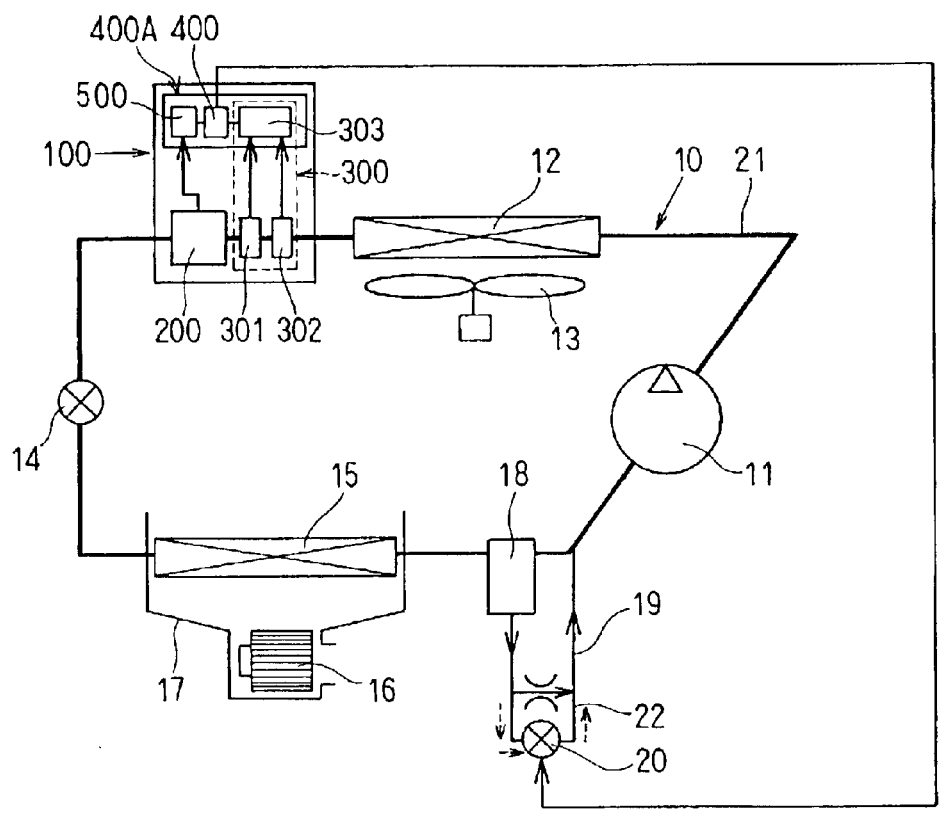
FIG. 15 is a schematic view that illustrates an overall view of a configuration of a sixth embodiment of the invention.

FIG. 15 shows a sixth embodiment of the present invention. In this embodiment, the oil content measuring device 100 itself is installed in the refrigerating system 10. The refrigerating system 10 is constructed such that the amount of the lubricating oil to be supplied from the accumulator 18 to the compressor 11 is appropriately controlled on the basis of the value of the obtained oil content χ.

The basic configuration of the sixth embodiment is the same as that of the first embodiment, except for a lubricating oil returning flow channel 19 through which the lubricating oil can be fed from the accumulator 18 to the compressor 11 and a bypass flow channel 22 going around the flow channel 19 and having an electromagnetic valve 20 for adjusting the amount of the lubricating oil to be fed by the bypass flow channel 22. Here, when the electromagnetic valve 20 is opened, the area of the flow channel may be increased such that the amount of the lubricating oil passing through the bypass flow channel 22 is larger than the amount of the lubricating oil passing through the flow channel 19.

Then, the computing device 400 of the oil content measuring device 100 is designed such that it stores the predetermined oil content χlow which is provided as a reference value for deciding to open the above electromagnetic valve 20. It can be compared with the oil content χs to be measured whenever necessary by the oil content determining device 500.

Figure 16:
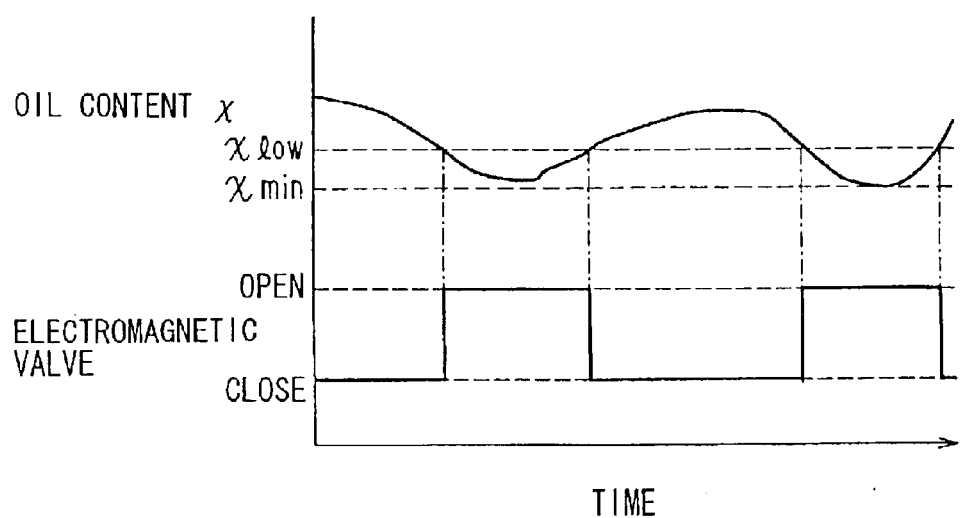
FIG. 16 is a time chart for illustrating an open and close state of the electromagnetic valve with respect to the change in oil content.

Then, as shown in a time-chart of FIG. 16, if the oil content χs is lower than the predetermined oil content χlow, then the electromagnetic valve 20 is opened. If the oil content χs is higher than the predetermined oil content χlow, then the electromagnetic valve 20 is closed. Therefore, the compressor 11 is allowed to securely receive a supply of the required amount of lubricating oil (with the oil content χmin).

Figure 17A:
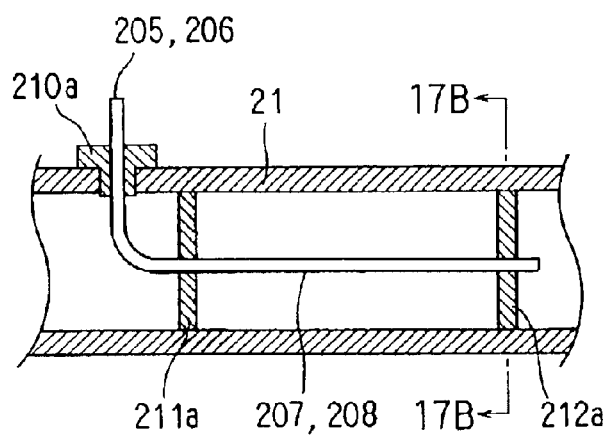
FIG. 17A is a cross-sectional schematic view illustrating the electrodes of a third variation of the sixth embodiment of the present invention.
Figure 17B:
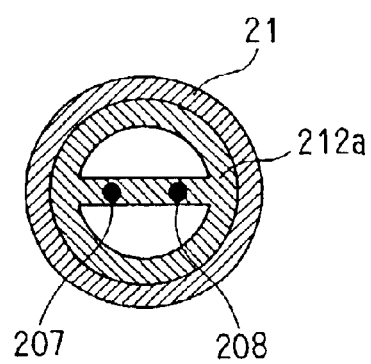
FIG. 17B is a cross-sectional view taken along the line 17B—17B in FIG. 17A illustrating the electrodes of a third variation of the sixth embodiment of the present invention.

Furthermore, in the refrigerating system 10 in which such an oil content measuring device 100 is installed, each of the electrodes 207 and 208 of the electrostatic capacity measuring device 200 may be in the shape of a needle and, as shown in FIG. 17A, they may be arranged in the piping 21 through the insulators 210*a*, 211*a*, and 212*a*. FIG. 17B shows a cross-sectional view of the piping of FIG. 17A.

Therefore, the body parts 201 and 202 which can be provided as a case of the magnetic capacity measuring device 200 may be eliminated to make more space while reducing its manufacturing cost. In addition, the electrodes 207 and 208 are formed like needles for versatility of shape. That is, they can be arranged even on a bent portion or the like of the piping 21, resulting in an excellent mounting ability.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An oil content measuring device, comprising:

electrostatic capacity measuring means for measuring an electrostatic capacity of a refrigerant containing a refrigerating machine oil;

density measuring means for measuring a density of at least one of the refrigerant and the refrigerating machine oil;

computing means for computing correlation characteristics between the electrostatic capacity and an oil content using the density measured by the density measuring means, the oil content representing a ratio of an amount of the refrigerating machine oil to an amount of the refrigerant containing the refrigerating machine oil; and oil content determining means for determining an oil content at a measuring time from an electrostatic capacity measured by the electrostatic capacity measuring means using the correlation characteristics obtained by the computing means.

2. The oil content measuring device according to claim 1, wherein the computing means performs a computation on the correlation characteristics between the electrostatic capacity and the oil content at temperature and pressure conditions at the time of the measurement by linear interpolation using a density of the refrigerant on the basis of a plurality of correlation characteristics between the electrostatic capacity and the oil content previously prepared under a plurality of temperature and pressure conditions.

3. The oil content measuring device according to claim 1, wherein the computing means performs a computation on the correlation characteristics between the electrostatic capacity and the oil content using an arithmetic expression previously defined such that the electrostatic capacity is determined by the oil content, a density of the refrigerant, and a density of the refrigerating machine oil.

4. The oil content measuring device according to claim 3, wherein the density measuring means includes a temperature detecting means for detecting a temperature of the refrigerant and pressure detecting means for detecting a pressure, and the density is calculated using detected values obtained respectively by the temperature detecting means and the pressure detecting means.

5. The oil content measuring device according to claim 1, wherein the density measuring means includes a temperature detecting means for detecting a temperature of the refrigerant and pressure detecting means for detecting a pressure, and the density is calculated using detected values obtained respectively by the temperature detecting means and the pressure detecting means.

6. The oil content measuring device according to claim 5, wherein the oil content is determined by replacing the electrostatic capacity with a relative dielectric constant divided by an electrostatic capacity in a vacuum.

7. The oil content measuring device according to claim 1, wherein the oil content is determined by replacing the electrostatic capacity with a relative dielectric constant divided by an electrostatic capacity in a vacuum.

8. The oil content measuring device according to claim 7, wherein each of the electrostatic capacity and the density is measured at a position in the vicinity of a suction side or a discharge side of a compressor that compresses the refrigerant.

9. The oil content measuring device according to claim 1, wherein each of the electrostatic capacity and the density is measured at a position in the vicinity of a suction side or a discharge side of a compressor that compresses the refrigerant.

10. The oil content measuring device according to claim 9, wherein a water repellent finish is applied to surfaces of electrodes of the electrostatic capacity measuring means when each of the electrostatic capacity and the density is measured at a position in the vicinity of the suction side of the compressor.

* * * * *